United States Patent
Xie et al.

(10) Patent No.: US 12,422,366 B2
(45) Date of Patent: Sep. 23, 2025

(54) NON-DESTRUCTIVE DETECTION OF EGG FRESHNESS BASED ON RAMAN SPECTROSCOPY

(71) Applicants: Yunfei Xie, Wuxi (CN); Yuliang Liu, Wuxi (CN); Hang Yu, Wuxi (CN); Weirong Yao, Wuxi (CN); Yahui Guo, Wuxi (CN); Yuliang Cheng, Wuxi (CN); Yichi Zhang, Wuxi (CN)

(72) Inventors: Yunfei Xie, Wuxi (CN); Yuliang Liu, Wuxi (CN); Hang Yu, Wuxi (CN); Weirong Yao, Wuxi (CN); Yahui Guo, Wuxi (CN); Yuliang Cheng, Wuxi (CN); Yichi Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 1216 days.

(21) Appl. No.: 17/214,809

(22) Filed: Mar. 27, 2021

(65) Prior Publication Data

US 2021/0247318 A1    Aug. 12, 2021

Related U.S. Application Data

(63) Continuation of application No. PCT/CN2020/072891, filed on Jan. 18, 2020.

(30) Foreign Application Priority Data

Jan. 9, 2020    (CN) .......................... 202010023268.2

(51) Int. Cl.
  *G01N 21/65*    (2006.01)
  *G01N 33/08*    (2006.01)
  *G06F 17/18*    (2006.01)

(52) U.S. Cl.
  CPC ............. *G01N 21/65* (2013.01); *G01N 33/08* (2013.01); *G06F 17/18* (2013.01)

(58) Field of Classification Search
  None
  See application file for complete search history.

(56) References Cited

FOREIGN PATENT DOCUMENTS

| | | |
|---|---|---|
| CN | 103424394 A | 12/2013 |
| CN | 109001152 A | 10/2018 |
| CN | 208752006   | 4/2019 |
| TW | 201913072 A | 4/2019 |

OTHER PUBLICATIONS

Giunchi, Alessandro, et al. "Non-destructive freshness assessment of shell eggs using FT-NIR spectroscopy." Journal of food engineering 89.2 (2008): 142-148. (Year: 2008).*
Kizil R, Irudayaraj J. Applications of Raman spectroscopy for food quality measurement. Nondestructive testing of food quality. Dec. 27, 2007:143-63. (Year: 2007).*
Afseth, Nils Kristian, Vegard Herman Segtnan, and Jens Petter Wold. "Raman spectra of biological samples: A study of preprocessing methods." Applied spectroscopy 60.12 (2006): 1358-1367. (Year: 2006).*
Ishigaki, Mika, Akinori Taketani, and Hidetoshi Sato. "Discrimination of fish egg quality and viability by Raman spectroscopy." Analytical methods 6.23 (2014): 9206-9211. (Year: 2014).*
Butler HJ, Ashton L, Bird B, Cinque G, Curtis K, Dorney J, Esmonde-White K, Fullwood NJ, Gardner B, Martin-Hirsch PL, Walsh MJ , McAinsh MR, Stone N, Martin FL. Using Raman spectroscopy to characterize biological materials. Nat Protoc. Apr. 2016;11(4):664-87. (Year: 2016).*
Galli R, Preusse G, Uckermann O, Bartels T, Krautwald-Junghanns ME, Koch E, Steiner G. In Ovo Sexing of Domestic Chicken Eggs by Raman Spectroscopy. Anal Chem. Sep. 6, 2016;88(17):8657-63. (Year: 2016).*
Q. Zhao et al. "Potential use of spectroscopic techniques for assessing table eggs and hatching eggs". Worlds Poultry Science Journal. 2019. 3(75): 447-450.
Xuefeng Shi et al. "Effects of chicken breeds, age, storage time, storage condition on the quality of egg cuticle". China Poulty. 2018. 40(17): 35-39.
Yaling Zhou. "Study of the characteristics of color change during the storage of cold fresh beef based on Raman spectroscopy". Student Dissertation. May 25, 2018.
Jiewen Zhao et al. "Visible-near-infrared transmission for rapid analysis of the freshness of eggs". Laser and Optoelectronics Progress. 2013. 50: 053003.

* cited by examiner

*Primary Examiner* — Olivia M. Wise
*Assistant Examiner* — Jonathan Edward Hayes
(74) *Attorney, Agent, or Firm* — Lili Chen

(57) ABSTRACT

Disclosed is a method for non-destructive detection of egg freshness based on Raman spectroscopy technology, which belongs to the field of food detection. Partial least squares regression models are built using Raman spectroscopic data and measured values of physicochemical indexes for egg freshness, which can be used to predict egg freshness based on Raman spectrum of egg shell surface. The Raman spectroscopic data are collected in the waveband of 100-3000 $cm^{-1}$. The physicochemical indexes used in the invention include the Haugh unit, the albumen pH, the air chamber diameter and the air chamber height. By using the partial least squares model, values of physicochemical index for egg freshness can be obtained from Raman spectra collected on egg shell surfaces, thus achieving the goal of non-destructive detection of egg freshness.

4 Claims, 2 Drawing Sheets

NON-DESTRUCTIVE DETECTION OF EGG FRESHNESS BASED ON RAMAN SPECTROSCOPY

CROSS-REFERENCE TO RELATED APPLICATIONS

This application is a continuation of international application PCT/CN2020/072891, filed Jan. 18, 2020, which claims the benefit of priority to Chinese patent application No. CN2020100232682, filed Jan. 9, 2020, the content of which is hereby incorporated by reference in its entirety.

BACKGROUND OF THE INVENTION

Field of the Invention

The disclosure relates to the field of food examination, and in particular to a method for non-destructive detection of egg freshness based on Raman spectroscopy.

Description of the Related Art

As a highly nutritious food, eggs can provide the human body with essential nutrients such as protein, fat, minerals and vitamins. However, because eggs are particularly prone to corruption and deterioration during production, processing, sales and circulation, which will not only harm the economic interests of producers, but even endanger the health of consumers, the study of egg freshness has important and significant value.

At present, detection indexes of egg freshness mainly include the Haugh unit, the albumen pH value, the air chamber diameter, the air chamber height, etc., but these indexes can only be obtained through destructive testing methods.

With the advancement of technology, non-destructive testing has been applied to all aspects. Currently, the non-destructive testing techniques applied to egg freshness mainly include infrared spectroscopy, hyperspectral, electronic nose, sonic pulse, machine vision technology, impedance method, etc. There is no non-destructive testing method using Raman spectroscopy.

SUMMARY OF THE INVENTION

In an embodiment of the invention, it provides a method for non-destructive detection of egg freshness based on Raman spectroscopy, which uses Raman spectral data and four physicochemical indexes for egg freshness to build respective partial least squares regression models.

The Raman spectral data used in the method is the Raman spectrum intensity of an egg shell surface in a range of 100-3000 $cm^{-1}$.

The freshness physicochemical indexes include the Haugh unit, the albumen pH, the air chamber diameter and the air chamber height.

In an embodiment of the invention, the partial least squares regression model is built as follows:
(1) acquiring the Raman spectrum intensity of the egg sample in the range of 100-3000 $cm^{-1}$, and measuring the corresponding values of the four physicochemical indexes of the egg sample; and
(2) establishing partial least squares regression models using the acquired Raman spectral data and each of the four physicochemical indexes.

In an embodiment of the invention, the Raman spectral data further undergoes pretreatment before modeling. The pretreatment includes using any one or more methods selected from the following: Savitzky-Golay smoothing (SG), normalization (NL), first derivative ($1^{st}$ Der), second derivative ($2^{nd}$ Der), baseline correction (BL), standard normal variable transformation (SNV), multiplicative scatter correction (MSC) and denoise (Denoise).

In an embodiment of the invention, when the partial least squares regression model is built between the Raman spectral data and the Haugh unit, the pretreatment method is preferably $2^{nd}$ Der.

In an embodiment of the invention, when the partial least squares regression model is built between the Raman spectral data and the albumen pH, the pretreatment method is preferably $2^{nd}$ Der.

In an embodiment of the invention, when the partial least squares regression model is built between the Raman spectral data and the air chamber diameter, the pretreatment method is preferably $1^{st}$ Der.

In an embodiment of the invention, when the partial least squares regression model is built between the Raman spectral data and the air chamber height, the pretreatment method is preferably $1^{st}$ Der.

In an embodiment of the invention, methods of measuring the reference values of the four physicochemical indexes are as follows: measuring the Haugh unit of an egg by an egg product analyzer; measuring the albumen pH by a pH meter; and measuring the air chamber diameter and the air chamber height by a vernier caliper.

In an embodiment of the invention, the Raman spectral data used for modeling can be data acquired at a single position or average data of Raman spectra acquired at three different positions. The three acquisition positions are the egg top, the egg shell bottom and the egg waist. Two points are selected from each acquisition position, and each point is measured for 3 times to obtain an average value of the point.

In an embodiment of the invention, the egg top refers to the small end position of the egg, the egg bottom refers to the big end position of the egg, and the egg waist refers to the middle line position of the egg.

In an embodiment of the invention, the acquired Raman spectral data is preferably the Raman spectrum intensity on the egg shell surface at the egg top in the range of 100-3000 $cm^{-1}$.

In an embodiment of the invention, building the partial least squares regression model comprises the following steps:
(1) data acquisition: acquiring the Raman spectrum and measuring corresponding freshness physicochemical indexes of each egg; and
(2) data modeling: building respective partial least squares regression models between the acquired Raman spectrum and each of the measured four freshness physicochemical indexes of the Haugh unit, the egg albumen pH, the air chamber diameter and the air chamber height. According to the built models, values of freshness physicochemical indexes of a sample egg can be directly obtained through acquired Raman spectrum without destruction of the egg, thus providing a non-destructive, fast and accurate method for testing egg freshness.

In an embodiment of the invention, the egg sample is stored in a constant-temperature and constant-humidity incubator, and data acquisition is performed every 2, 3, 4, 5, 6 or more days.

In an embodiment of the invention, the Raman spectrum on the egg shell surface is acquired through a portable Raman spectrometer.

In an embodiment of the invention, acquisition parameters of the Raman spectrum are as follows: the excitation wavelength is 785 nm; the acquisition waveband is 100-3000 $cm^{-1}$; the acquisition time is 5 s; the acquisition is performed for 3 times; and the distance from a detection probe to the egg shell surface is 6 mm.

In an embodiment of the invention, the Raman spectrum intensities acquired from each position of three collection positions are used as representative Raman spectrum intensities of the respective position. Alternatively, average values of Raman spectrum intensities acquired from the three collection positions are used as overall average Raman spectrum intensities. Models can be built between the representative Raman spectrums and each of the four physicochemical indexes. Alternatively, models can be built between the overall average Raman spectrum and each of the four physicochemical indexes.

In an embodiment of the invention, the models are built based on a partial least squares regression method. 80% of samples are used as a model-building set, and 20% of samples are used as a testing set.

The invention establishes a relationship between the Raman spectrum of egg surface and the physicochemical indexes of egg freshness so as to predict the physicochemical indexes of egg freshness using Raman spectra. As a method suitable for on-site detection, Raman spectroscopy has the advantages of rapidity and simplicity. At the same time, Raman spectroscopy can provide information about the vibration frequency of chemical molecules. The present invention provides a non-destructive method for testing egg freshness based on Raman spectroscopy.

The acquired Raman spectrum not only contains the information of the sample itself, but also some other irrelevant information, such as fluorescence background, noise and stray light. Therefore, it is necessary to pre-process the acquired Raman spectra of eggs to select informative spectral data and reduce the interference from irrelevant signals. This invention uses 8 pre-processing methods, namely, curve smoothing (SG), normalization (NL), first-order derivative ($1^{st}$ Der-SG), second-order derivative ($2^{nd}$ Der-SG), and baseline correction (BL).), standard normal variable transformation (SNV), multivariate scattering correction (MSC), noise reduction (Denoise). It is cumbersome and time-consuming to collect Raman spectra at many different locations. After comparison of the spectral modeling effects of different acquisition locations, the optimal locations are determined to be at the top, the bottom and the waistline of an egg sample.

The invention provides a non-destructive method for testing egg freshness based on Raman spectrum. In the present invention, the correlation coefficients of the best prediction models established on the basis of existing data are all 0.8 or higher, and the correlation coefficients of the models for haugh units, albumen pH value and air cell diameter can reach 0.9 or higher, indicating a good prediction capability of the prediction models that can predict egg freshness based on Raman spectra of the egg shell surface. By expanding the spectrum database with more experimental data, the performance of the prediction model can be further improved. The Raman spectrum method of the present invention has the advantages of simplicity, rapidity as well as in situ detection. Compared with infrared spectroscopy methods, it can avoid the interference of water molecules on the spectral results. This method may also be applicable for testing the freshness of other foods.

DETAILED DESCRIPTION

Figure 1:
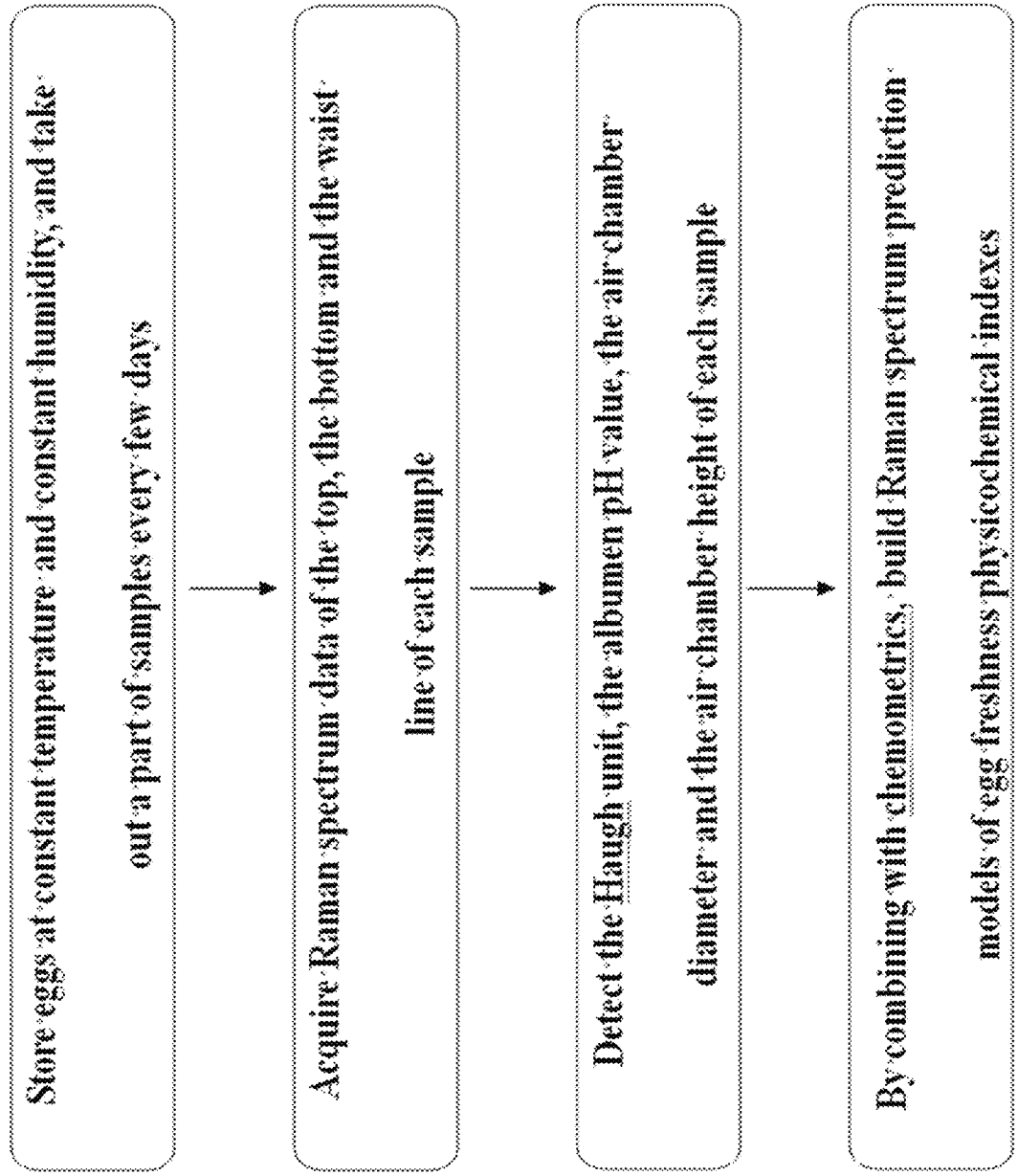
FIG. 1 is a flow diagram of a method for non-destructive detection of egg freshness based on Raman spectroscopy.
Figure 2:
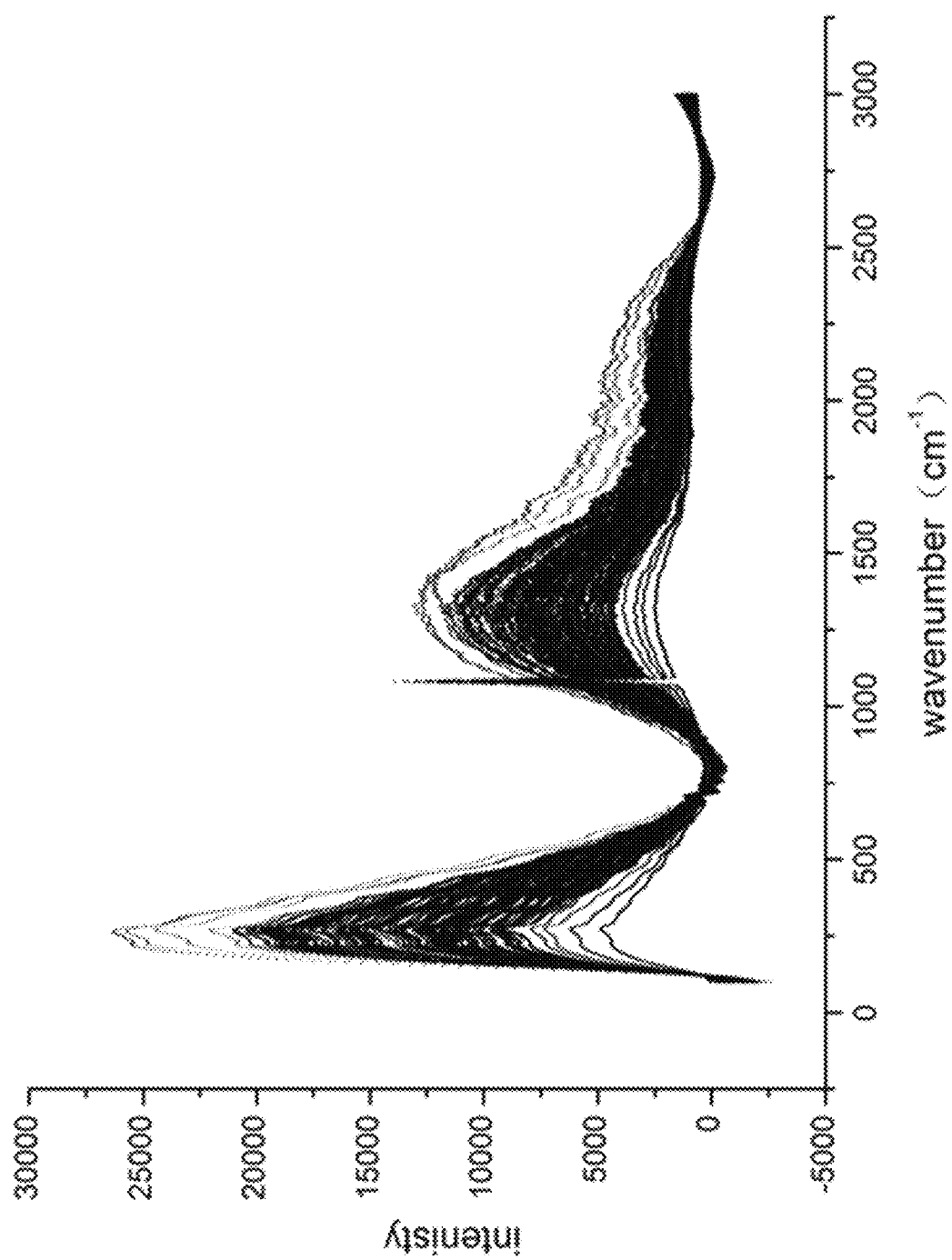
FIG. 2 is a schematic diagram of an overall average Raman spectrum of an egg sample.

Specific embodiments of the invented method are described in detail with regard to the drawings and the Examples. The specific embodiments are presented here for illustrative purposes only, and are not meant to limit the scope of the invention, which is defined by the claims as presented. Various changes and modifications to the disclosed methods known to those skilled in the art shall be covered within the scope of protection.

Haugh unit: a measure of egg freshness that is calculated according to the formula, $HU=100 \times lg(H+7.57-1.7 \times G^{0.37})$, wherein HU is the Haugh unit; H is the egg albumen height, in mm; and G is the mass of a whole egg, in gram.

Measurement of Albumen pH: an egg albumen pH value is measured by a pH meter after the egg albumen is separated into a flask and is uniformly stirred by a glass rod.

Measurement of Air chamber diameter and air chamber height: the air chamber diameter and the air chamber height are measured by a vernier caliper from the inside of an egg after the egg is broken and a complete air chamber is remained; and the unit of the air chamber diameter and the air chamber height is mm.

Example 1. Building of Raman Spectrum Prediction Models (1) Egg samples: Firstly, a batch of freshest eggs was bought. The eggs selected in the present example was HY-LINE brown eggs, the chicken age was 200 days, the eggs were stored in a 20° C. and 40% RH constant-temperature and constant-humidity incubator, and a portion of the eggs were taken out for data acquisition every 3 days.

(2) Acquisition of Raman spectrum of each sample: Raman spectral data of the top, the bottom and the waist line of the sample was acquired by a portable Raman spectrometer, two points were selected at each position, and each point was repeatedly tested for 3 times. Raman detection parameters were as follows: the integral time was 5 s, scanning was performed for 3 times, the acquisition waveband was the full waveband of 100-3000 $cm^{-1}$, and the distance from a probe to the egg shell surface was 6 mm. Corresponding Raman spectral data was measured.

(3) Detection of the reference value of each physicochemical index of each sample: The Haugh unit of the eggs was detected by an egg product analyzer. The albumen pH was measured by a pH meter. The air chamber diameter and the air chamber height were measured by a vernier caliper. Reference values of the Haugh unit, the egg albumen pH, the air chamber diameter and the air chamber height were respectively acquired.

(4) Data modeling analysis: By combining with chemometrics, the measured Raman spectrum intensity data of the eggs in the full waveband of 100-3000 $cm^{-1}$ was utilized to build partial least squares regression (PLSR) models, i.e., Raman spectrum prediction models of egg freshness physicochemical indexes, with the reference value of each of the physicochemical indexes respectively.

The Raman spectrum prediction models were partial least squares regression models built by using the partial least squares regression method. 80% of samples in test samples were used as a correction set, and 20% of samples were used as a prediction set (where the correction set was samples for building a model structure and parameters, and the prediction set was samples for evaluating the model robustness and prediction performance). It should be ensured that the data range of the prediction set are within the data range of the correction set, and additionally, the difference between average values of the correction set and the prediction set was not too big. Different-set data of the example was shown in Table 1.

TABLE 1

Different-set statistical data of each physicochemical index

| Index | Sample | Sample quantity | Minimum value | Maximum value | Average value | Standard deviation SD |
|---|---|---|---|---|---|---|
| Haugh unit | Correction set | 100 | 42.7 | 82.7 | 62.2 | 7.1 |
| | Prediction set | 25 | 49.4 | 79.4 | 61.5 | 7.4 |
| Egg albumen pH | Correction set | 100 | 8.78 | 9.45 | 9.26 | 0.15 |
| | Prediction set | 25 | 8.81 | 9.45 | 9.27 | 0.15 |
| Air chamber diameter | Correction set | 100 | 15.47 | 44.91 | 32.01 | 5.82 |
| | Prediction set | 25 | 18.20 | 43.17 | 30.20 | 5.21 |
| Air chamber height | Correction set | 100 | 2.19 | 22.12 | 8.96 | 4.28 |
| | Prediction set | 25 | 2.22 | 18.74 | 9.05 | 4.17 |

In this example, an average value of the Raman spectra acquired from all positions of the egg was used as an overall average spectrum to build full waveband PLSR models with each of four physicochemical indexes. Results were shown in Table 2.

TABLE 2

Modeling results of original Raman spectrum and each physicochemical index

| Index | Main component number | Rc | RMSEC | Rp | RMSEP |
|---|---|---|---|---|---|
| Haugh unit | 6 | 0.664 | 5.326 | 0.520 | 6.541 |
| Egg albumen pH | 6 | 0.832 | 0.083 | 0.846 | 0.081 |
| Air chamber diameter | 6 | 0.767 | 3.734 | 0.822 | 3.629 |
| Air chamber height | 3 | 0.630 | 3.324 | 0.822 | 2.494 |

In Table 2, Rc represents the correlation coefficient of the correction set; RMSEC represents the root-mean-square error of the correction set; Rp represents the correlation coefficient of the prediction set; and RMSEP represents the root-mean-square error of the prediction set.

From Table 2, it can be seen that the correlation coefficient of the model built by the unpretreated average Raman spectrum and the egg albumen pH value could reach 0.6 or higher, and could reach 0.8 or higher under better conditions. This shows that the model had good prediction performance. Additionally, the correlation coefficients of the models built with other three physicochemical indexes were all 0.6 or higher. If the spectrum is pretreated, it is possible to obtain a model with more stable and better prediction performance.

Example 2. Influence of Different Raman Spectrum Pretreatments on Modeling

Referring to Example 1, the average value of all Raman spectra acquired from three detection positions was used as the overall average Raman spectrum, and the overall average Raman spectrum was respectively subjected to the following pretreatment: Savitzky-Golay smoothing (SG), normalization (NL), first derivative ($1^{st}$ Der), second derivative ($2^{nd}$ Der), baseline correction (BL), standard normal variable transformation (SNV), multiplicative scatter correction (MSC) and denoise (Denoise). Taking the Haugh unit value as an example, full waveband PLSR modeling results were as shown in Table 3.

TABLE 3

Influence of different Raman spectrum pretreatment methods on model performance

| Pretreatment mode | Main component number | Rc | RMSEC | Rp | RMSEP |
|---|---|---|---|---|---|
| Raw | 6 | 0.664 | 5.326 | 0.520 | 6.541 |
| SG | 6 | 0.632 | 5.524 | 0.504 | 6.495 |
| NL | 6 | 0.646 | 5.439 | 0.659 | 5.714 |
| $1^{st}$ Der | 5 | 0.874 | 3.463 | 0.790 | 4.566 |
| $2^{nd}$ Der | 6 | 0.908 | 2.985 | 0.842 | 4.026 |
| BL | 6 | 0.648 | 5.427 | 0.517 | 6.521 |
| SNV | 6 | 0.491 | 5.085 | 0.629 | 5.899 |
| MSC | 6 | 0.699 | 5.097 | 0.630 | 5.890 |
| Denoise | 6 | 0.925 | 2.708 | 0.325 | 7.363 |

Further, the effects of the pretreatment methods was determined on models between the overall average Raman spectrum and each physicochemical index. Using only one pretreatment method, an optimal Raman spectrum pretreatment method of each physicochemical index model was obtained. For the Haugh unit and albumen pH value modeling, the optimal Raman spectrum pretreatment method was $2^{nd}$ Der, and for the air chamber diameter and the air chamber height modeling, the optimal pretreatment method was $1^{st}$ Der. If more than one of the pretreatment methods are combined, the modeling performance may be better.

Example 3. Influence of Different Raman Measuring Positions on Modeling

This example tested the effect of Raman spectrum acquisition position on the modeling performance. The Raman spectrum acquisition positions were selected to be the egg top, the egg bottom and the egg waist. The egg top refers to a small end position of the egg. The egg bottom refers to a big end position of the egg. The egg waist refers to a middle line position of the egg. Two spots were selected for each acquisition position, and three Raman spectra were acquired at each spot.

The average value of the Raman spectra acquired from each acquisition position are used as representative Raman spectrum of the respective position. The representative Raman spectrum of the three acquisition positions were respectively pretreated by the optimal pretreatment method as determined in Example 2. Results of full waveband PLSR models built with the four physicochemical indexes at different positions were as shown in Table 4.

TABLE 4

Performance of PLSR Models of representative Raman spectra at different positions

| Index | Pretreatment method | | Top | Bottom | Waist | Average |
|---|---|---|---|---|---|---|
| Haugh unit | $2^{nd}$ Der | Rc | 0.944 | 0.934 | 0.930 | 0.908 |
|  |  | Rp | 0.925 | 0.751 | 0.794 | 0.842 |
| Egg albumen pH | $2^{nd}$ Der | Rc | 0.945 | 0.936 | 0.936 | 0.940 |
|  |  | Rp | 0.935 | 0.948 | 0.927 | 0.941 |
| Air chamber diameter | $1^{st}$ Der | Rc | 0.903 | 0.854 | 0.870 | 0.872 |
|  |  | Rp | 0.915 | 0.914 | 0.882 | 0.902 |
| Air chamber height | $1^{st}$ Der | Rc | 0.828 | 0.764 | 0.815 | 0.817 |
|  |  | Rp | 0.830 | 0.829 | 0.834 | 0.826 |

The best testing methods for the HY-LINE brown eggs of 200-day-old chicken, includes: the Raman spectrum was acquired from the egg top; the Raman spectrum was pretreated by $2^{nd}$ Der or $1^{st}$ Der method; full waveband PLSR models of 100-3000 cm$^{-1}$ were built using the pretreated Raman spectral data and measured values of the egg freshness physicochemical indexes. As shown from Table 4, the PLSR models achieved good predictive performance. For the model of the Haugh unit value, Rc was 0.944 and Rp was 0.925. For the model of the albumen pH value, Rc was 0.945 and Rp was 0.935. For the model of the air chamber diameter, Rc was 0.903 and Rp was 0.915. For the model of the air chamber height, Rc was 0.828 and Rp was 0.830.

Comparative Example 1

When performing non-destructive measurement of other egg freshness indexes (such as yolk index) of the HY-LINE brown eggs or other types of eggs based on Raman spectroscopy, one can refer to the methods and procedures provided herein.

Referring to operation steps of Example 1, Raman spectral data of egg samples was collected through steps (1)-(2), and the measured values of the physicochemical indexes in the step (3) were replaced with values of the yolk index.

The process of measuring the yolk index was as follows: an egg was broken onto a plane; and the height and the diameter of the yolk were measured by a vernier caliper. The yolk index was calculated by the formula, yolk index=yolk height/yolk diameter (the unit of the yolk height and the yolk diameter is mm).

(4) Data modeling analysis: the collected Raman spectral data of the egg in the full waveband of 100-3000 cm$^{-1}$ was utilized to build partial least squares regression models with the measured values of yolk index.

Before any pretreatment, the Rc for the PLSR model between the average Raman spectrum and yolk index only reached 0.366. After the spectrum pretreatment, the Rc for the best PLSR model between the average Raman spectrum and yolk index reached 0.569. It thus showed that PLSR model based on the Raman spectrum is not suitable for modeling the yolk index.

What is claimed is:

1. A method for non-destructive detection of egg freshness, comprising:
   (1) acquiring Raman spectral data on surfaces of sample eggs;
   (2) measuring values of a physicochemical index for egg freshness of the sample eggs, wherein the physicochemical index for egg freshness is Haugh unit, albumen pH, air chamber diameter or air chamber height;
   (3) pretreating the Raman spectral data using selected pretreatment methods, wherein the pretreatment method is first derivative for predicting physicochemical values of air chamber diameter or air chamber height, and wherein the pretreatment method is second derivative for predicting values of Haugh unit or albumen pH,
   (4) building a partial least squares regression (PLSR) model using the pretreated Raman spectral data and the measured values of the physicochemical index; and
   (5) using the PLSR model and a Raman spectrum of a test egg to obtain a value of the physicochemical index and using the obtained physicochemical index value to detect the freshness of the test egg without breaking the test egg,
   wherein parameters for acquiring the Raman spectral data are as follows: excitation wavelength is 785 nm, acquisition waveband is 100-3000 cm$^{-1}$, acquisition time is 5 s, the acquisition is performed for 3 times, and distance from a probe to the egg surface is 6 mm.

2. The method of claim 1, wherein a position for acquiring Raman spectral data is egg top, egg bottom or egg waist.

3. The method of claim 2, wherein the Raman spectral data used for building the PLSR model are Raman spectral data acquired at a single position.

4. The method of claim 2 wherein the Raman spectral data used for building the PLSR model are average data of three Raman spectral data acquired at the three positions.

* * * * *